United States Patent
Beals

(10) Patent No.: US 6,524,296 B1
(45) Date of Patent: *Feb. 25, 2003

(54) VESSEL CANNULA HAVING PROPERTIES VARYING ALONG THE AXIAL LENGTH

(75) Inventor: Brian S. Beals, East Grand Rapids, MI (US)

(73) Assignee: Medtronic, Inc., Minneapolis, MN (US)

(*) Notice: Subject to any disclaimer, the term of this patent is extended or adjusted under 35 U.S.C. 154(b) by 0 days.

This patent is subject to a terminal disclaimer.

(21) Appl. No.: 08/840,837

(22) Filed: Apr. 17, 1997

(51) Int. Cl.[7] .............................................. A61M 31/00
(52) U.S. Cl. ...................... 604/500; 604/257; 604/264
(58) Field of Search ................................. 604/264, 272, 604/175, 95, 6.14, 6.16, 500, 257, 523

(56) References Cited

U.S. PATENT DOCUMENTS

| | | | |
|---|---|---|---|
| 3,769,975 A | * | 11/1973 | Nimoy et al. |
| 4,044,757 A | * | 8/1977 | McWhorter et al. |
| 5,146,925 A | * | 9/1992 | Snow |
| 5,236,417 A | * | 8/1993 | Wallis |
| 5,246,430 A | * | 9/1993 | MacFarlane |
| 5,308,342 A | | 5/1994 | Sepetka et al. |
| 5,364,374 A | * | 11/1994 | Morrison et al. |
| 5,478,309 A | | 12/1995 | Sweezer et al. |
| 5,489,269 A | * | 2/1996 | Aldrich et al. |
| 5,573,521 A | * | 11/1996 | MacFarlane |
| 5,668,912 A | * | 9/1997 | Keller |

FOREIGN PATENT DOCUMENTS

| | | | |
|---|---|---|---|
| DE | 00 76501 | * | 5/1919 |
| EP | 612536 | | 8/1994 |
| WO | WO 91/07203 | | 5/1991 |
| WO | WO 97/39789 | | 10/1997 |

OTHER PUBLICATIONS

Microgroup http://www.microgroup.com/project/shtab.htm (print out), May 25, 2000.*
Microgroup http://www.microgroup.com/project/sstub.htm (print out), May 25, 2000.*
Microgroup http//www.microgroup.com/project/smg-tab.htm (print out), May 25, 2000.*
"Polymers: Structure and Properties" C. A. Daniels Technomic Publishing Co. Lancaster P.A., 1989.*
"Standard Handbook for Mechanical Engineers" Mechanical Properties of Materials, unknown pp. 5:6 & 6:193, unknown.*
Translation of German–Austria Pat Specification 76501, May 1919.*
Medtronic–DLP Product Catalog, fourth edition, 1996, three pages.
Copyright 1996 Medtronic DLP, DLP Product Catalog, Fourth Edition, p. 58.
Copyright Jul., 1996 Medtronic, Inc., Minimally Invasive Cardiac Surgery, A Primer.
PCT, International Search Report, mailing date Aug. 8, 1998 for International Application No. PCT/US 98/07860.

* cited by examiner

Primary Examiner—Mark Bockelman
(74) Attorney, Agent, or Firm—Foley & Lardner

(57) ABSTRACT

A vessel cannula having properties varying along the axial length thereof is shown. In one embodiment, the cannula has a relatively rigid distal portion and a relatively flaccid, pliable, proximal portion and a lumen extending through both the rigid and flaccid portions. A cannula with this structure is ideally suited for use in minimally invasive cardiac surgical procedures when it is desired to perform a distal perfusion of a coronary artery.

30 Claims, 1 Drawing Sheet

VESSEL CANNULA HAVING PROPERTIES VARYING ALONG THE AXIAL LENGTH

BACKGROUND OF THE INVENTION

1. Field of the Invention

This invention relates to a vessel cannula and, more particularly, to a cannula having varying properties, such as rigidity or resistance to deflection, along its axial length. In one aspect, the vessel cannula has one relatively rigid portion and a second portion which is more pliable than the rigid portion. This cannula is ideally suited for use in minimally invasive cardiac surgical procedures but can be adapted for use in any fluid conducting application.

2. Description of the Related Art

Vessel cannula have long been used during surgical procedures, such as cardiac surgery. The cannula are typically used to provide a fluid flow path into, out of, or through a vessel, such as a coronary artery. An example of a known cannula is seen in FIG. 1 (prior art) which represents an arteriotomy cannula commercially available from the DLP Division of Medtronic, Inc. This cannula comprises a body portion A having a lumen B extending therethrough with a bulb C provided at the distal end thereof and a female luer connector D provided at the proximal end thereof. The bulb C and rigid body A are integrally molded as a single unit whereas the luer connector D is molded independently of the body and secured thereto by conventional means.

The cannula seen in FIG. 1 (prior art) is ideally suited for use in an open heart surgical procedure because the surgeon can easily place the cannula in the operative position in view of the size of the chest wall opening.

A growing surgical trend is to move away from traditional open heart surgical procedures to more less traumatic minimally invasive cardiac surgical procedures. However, known surgical equipment such as the cannula 3seen in FIG. 1 is not well adapted for these minimally invasive surgical techniques. During most minimally invasive surgical techniques, the size of the surgical incision in the chest wall is dramatically reduced, thereby requiring maximum efficiency in the positioning and operation of the necessary surgical equipment. The structure of the known cannula may not be best suited for use in these procedures. An arteriotomy cannula used in a minimally invasive surgical procedure must have sufficient rigidity to be insertable into the coronary artery and yet have sufficient flexibility so that the cannula will not interfere with other surgical tools inserted through the relatively small chest wall opening.

SUMMARY OF THE INVENTION

The vessel cannula according to the invention overcomes the prior art by providing a cannula structure which has sufficient rigidity on the distal end thereof to permit insertion into the desired vessel and sufficient flexibility adjacent the proximal end thereof to permit easy movement and manipulation of the proximal end of the cannula after the distal end has been properly positioned in the vessel. Ideally, these problems are overcome by creating a cannula having properties such as rigidity which vary along the axial length thereof.

In a first aspect, the invention is directed to a cannula having two distinct body portions. The first body portion has a proximal end, a distal end, and a lumen formed therein extending between the proximal and distal ends. The first body portion has a prescribed rigidity or resistance to deflection identified as the first flexural rigidity. The second body portion similarly has a proximal end, a distal end, and a lumen formed therein extending between the ends. The proximal end of the second body portion is mounted to the distal end of the first body portion so that the lumens of the two portions are fluidly connected to one another. The second body portion similarly has a prescribed rigidity or resistance to deflection, different from the first, which is identified as the second flexural rigidity. The cannula is designed so that the second body portion is more rigid and less easily deformed or deflected than the first body portion. In the preferred embodiment, the first body portion has a flexural rigidity in the range of $3 \times 10^{-3}$ lb·in$^2$ to 50 lb·in$^2$, and the second body member has a rigidity in the range of $1 \times 10^{-4}$ to $4 \times 10^{-3}$ lb·in$^2$.

A cannula having this structure is ideally suited for use in a minimally invasive surgical procedure whereby the size of the opening in the patient's chest is dramatically smaller than the wound typically created for traditional open heart surgical procedures. With this structure, the distal end of the second body portion can be inserted into the coronary artery while the proximal end of the first body portion is positioned outside the patient's body. Preferably, the second body portion is dimensioned so that when the distal end is properly mounted in the coronary artery, the proximal end of the more rigid second body portion does not extend significantly above the surface of the patient's skin adjacent the chest wound. In addition, the first body portion preferably lays down across the patient's chest, thereby avoiding potential interference with surgical tools and procedures.

BRIEF DESCRIPTION OF THE DRAWINGS

The invention will now be described with reference to the drawings in which.

DETAILED DESCRIPTION OF THE PREFERRED EMBODIMENTS

Figure 1:
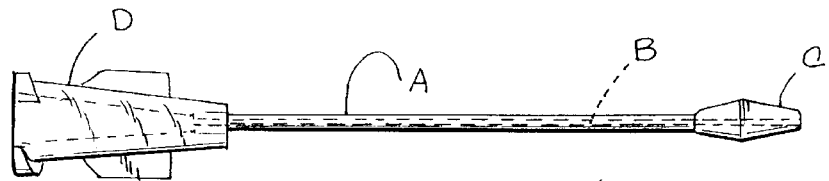
FIG. 1 is a top, plan view of a prior art vessel cannula.
Figure 2:
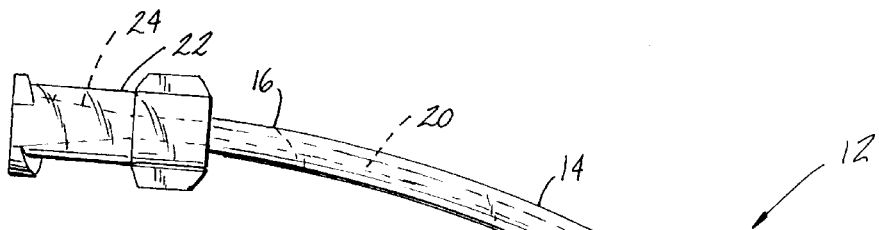
FIG. 2 is a top, plan view of the vessel cannula according to the invention.
Figure 3:
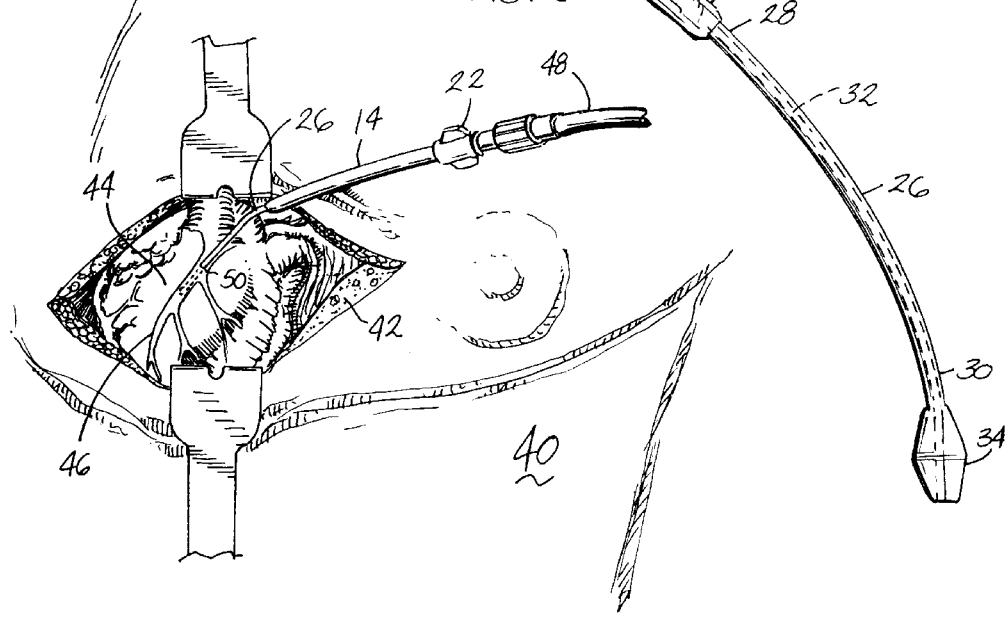
FIG. 3 is a plan view of a patient undergoing a minimally invasive cardiac surgical procedure with the cannula as seen in FIG. 2 in the operative position.

Referring now to the drawings and specifically, FIGS. 2 and 3, a cannula 12 according to the invention is shown. The cannula 12 comprises a first body portion 14 having a proximal end 16, a distal end 18, and a lumen 20 extending between the proximal 16 and distal ends 18. A conventional female luer connector 22 having a lumen 24 extending therethrough is securely mounted to the proximal end 16 of the first body portion 14. The cannula 12 also comprises a second body portion 26 having a proximal end 28, a distal end 30, and a lumen 32 extending between the proximal 28 and distal ends 30. Preferably, the proximal end 28 of the second body portion 26 is securely mounted to the distal end 18 of the first body portion 14. In addition, a bulb 34 is preferably integrally molded into the distal end 30 of the second body portion 26. The first body portion 14, luer connector 22, and second body portion 26 are mounted to one another so that the lumens of these respective elements create a fluid flow path extending through the cannula 12.

The first body portion 14 and second body portion 26 have differing properties to accommodate specific applications of the cannula 12. Specifically, the second body portion 26 is preferably more rigid and less easily deformed than the first body portion 14. The first body portion 14 is formed of a soft, pliable material such as polyvinyl chloride (PVC) or Krayton rubber. Conversely, the second body portion 26 is more rigid and less easily deformed than the first body portion 14. Preferably, the second body portion 26 is formed from a more rigid plastic such as urethane or a metal such as stainless steel. With this structure, the cannula 12 has a more rigid distal end and a more flexible, flaccid portion intermediate the rigid portion and the luer connector 22. This cannula 12 is ideally suited for a wide variety of surgical applications, one of those being minimally invasive cardiac surgery.

One criteria that can be used for selecting appropriate materials and dimensions for the first and second portions is calculating the flexural rigidity of the components. This characteristic of the product is calculated as follows:

$$Fr = E \cdot I \text{ (in units of lb·in}^2\text{)}$$

wherein Fr is the flexural rigidity

E is the modulus of elasticity in the units of lb·in$^2$

I is the area moment of inertia as described in the units in$^4$.

For a cylindrical tube, the area moment of inertia is calculated as follows:

$$I = (r_1^4 - r_2^4)(\pi)/4$$

Through calculations and experimentation, it appears as if the more rigid second portion 26 of the catheter according to the invention can have a flexural rigidity in the range of $3 \times 10^{-3}$ lb·in$^2$ to 50 lb·in$^2$. Similarly, the softer, more pliable first portion 14 can have a flexural rigidity in the range of $1 \times 10^{-4}$ lb·in$^2$ to $4 \times 10^{-3}$ lb·in$^2$. For example, the stiffer, second portion 26 can be formed of a ticoflex which has a modulus of elasticity equal to 4,000 psi. When this material is used in a cannula having an exterior diameter of 0.075 inch and an interior diameter of 0.053 inch, this results in a flexural rigidity equal to $6 \times 10^{-3}$ lb·in$^2$. Utilizing similar radiuses, a stainless steel or rigid second portion would have a flexural rigidity equal to 41.

The flexural rigidity of the first portion 14 is preferably significantly less than the flexural rigidity of the more stiffer section. For example, the flexural rigidity of a PVC cannula having a modulus of elasticity equal to 100 psi is equal to $3 \times 10^{-3}$ lb·in$^2$ when the external diameter is 0.15 inch and the internal diameter is 0.072 inch. An even softer material suitable for the pliable first portion is a Krayton rubber having a modulus of elasticity of 20 psi and a durometer A measurement of 5. Utilizing the same dimensions for the cylindrical tube as provided in the above PVC example, a Krayton rubber product would have a flexural rigidity of $6 \times 10^{-4}$ lb·in$^2$.

The preferred embodiment of the cannula according to the invention utilizes urethane for the more rigid second portion 26 having a flexural rigidity of 6×10–3 lb·in$^2$ as calculated above and PVC for the more pliable first portion having a flexural rigidity of $3 \times 10^{-3}$ lb·in$^2$.

FIG. 3 shows a patient undergoing a minimally invasive cardiac surgical procedure performed through an anterior lateral thoracotomy. During most minimally invasive cardiac surgical procedures, a relatively small access incision is formed in the patient's chest wall. The size of the incision has been minimized to reduce the trauma suffered by the patient. Unfortunately, minimizing the incision also creates additional challenges for the surgeon. One of those challenges centers around distal perfusion of a blocked or restricted coronary artery.

Persons skilled in the art will easily understand that this particular surgical procedure and access site are merely one example of an application of the cannula according to the invention. The cannula can be used in virtually any surgical procedure, regardless of whether or not the procedure is a coronary surgical procedure or a minimally invasive surgical procedure.

FIG. 3 shows a patient 40 having a chest wall incision 42 formed between adjacent ribs immediately above the heart 44. The ribs are spread open to provide maximum access to the heart without excessively damaging the ribs and chest wall tissue. With the heart 44 so exposed, the coronary artery 46 can be easily accessed by the surgeon. When the surgeon is performing a coronary artery bypass graft, the surgeon typically pinches closed the coronary artery 46 upstream from the restriction. The closing of the artery 46 can be performed by a conventional suture or through the use of known clamps and the like. After the coronary artery 46 has been closed for an extended period of time, a surgeon may desire to perfuse the artery 46 at a point distal from the suture or blockage to prevent ischemia of the heart tissue typically perfused by the coronary artery. The cannula 12 according to the invention is ideally suited for performing such distal perfusion. First, the surgeon creates an anastomosis aperture 50 in the coronary artery 46 or some other opening therein downstream or distally from the suture and arterial restriction. Next, the surgeon grasps the more rigid second body portion 26 of the cannula 12 and inserts the distal end 30 of the second body portion 26 through the chest wall incision 42 and into the anastomosis aperture 50 of the coronary artery 46. Preferably, the bulb 34 provided on the distal end 30 of the second body portion 26 is slightly larger than the diameter of the anastomosis aperture 50 so that the bulb 34 and distal end 30 of the second body portion 26 are snugly received in the coronary artery 46 through the anastomosis aperture 50. As a person skilled in the art will understand, the second body portion 26 must have a certain rigidity or resistance to deflection in order to be successfully inserted into the coronary artery 46.

After the surgeon has successfully inserted the second body portion 26 into the coronary artery, the luer connector 22 is fluidly connected to a source of perfusion fluid 48. Typically, this fluid would comprise oxygenated blood flowing from an external oxygenator if the patient is on extracorporeal bypass. Alternatively, if the heart were still beating, the source of fluid could be the heart whereby the connector 22 is fluidly connected via a conventional catheter to an artery somewhere in the patient's own vasculature, preferably, the femoral artery.

As the distal portion of the coronary artery 46 is perfused, the pliable first body portion 14 of the cannula can be easily manipulated by the surgeon so that this portion of the cannula will not interfere with other surgical tools or the procedure which the surgeon is performing. If the entire length of the cannula were formed from a material having sufficient rigidity so that it can be inserted into the anastomosis aperture 50, then it is likely that the proximal end of the cannula would project upwardly and outwardly from the chest wall incision 42. This would likely interfere with the surgeon's ability to perform the necessary techniques through the limited chest wall incision 42. If the proximal end of the cannula were projecting upwardly and outwardly through the incision 42, then it may be more difficult to connect and adequately secure the catheter to the source of perfusion fluid 48. By using the cannula having properties varying along the axial length thereof, a relatively rigid distal portion can be provided so that the cannula can be properly inserted into the anastomosis aperture 50, and a more flaccid proximal portion can be provided so that the cannula will minimally interfere with the other surgical tools. Another unexpected result in utilizing a cannula 12 according to the invention is that the relatively pliable proximal portion of the cannula can operate as a shock absorber to prevent inadvertent dislodging of the more rigid distal end of the cannula 12 from the anastomosis aperture 50. If the catheter from the supply of perfusion fluid or the proximal end of the cannula were to be inadvertently bumped or moved, the pliable proximal portion of the cannula would deflect and absorb a limited amount of shock and movement before translating this movement to the more rigid distal end of the cannula positioned in the coronary artery 46.

In the preferred embodiment of the cannula 12, the length of the second body portion 26 is dimensioned so that the proximal end 28 of the second body portion 26 is positioned immediately adjacent the chest wall incision 42 when the distal end 30 of the second body portion 26 is properly positioned within the anastomosis aperture 50. With this structure, the surgeon can grasp the second body portion with his fingers or the appropriate surgical tool while manually inserting the distal end 30 into the anastomosis aperture 50. Ideally, the first body portion 14 is pliable enough so that this portion will merely lay down or drape over the surgical dressing surrounding the chest wall incision 42 once the distal end of the cannula 12 is properly received in the coronary artery 46.

In the preferred embodiment, two, separate, molded or extruded members having differing properties are joined to one another to create the cannula 12 according to the invention. While this is the preferred embodiment of the invention, a person skilled in the art will understand that a cannula formed from a single molded body is within the scope of the invention provided that the varying axial properties can be induced into the structure or material of the cannula body. In addition, while the structure of the cannula 12 according to the invention is ideally suited for minimally invasive surgical procedures, a person skilled in the art will clearly understand that the invention can easily be used in other nonminimally invasive applications.

Reasonable variation and modification are possible within the spirit of the foregoing specification and drawings without departing from the scope of the invention.

The embodiments for which an exclusive property or privilege is claimed are defined as follows:

1. A cannula comprising:
    a first body portion having a proximal end, a distal end, and a lumen formed therein extending between the proximal and distal ends, the first body portion having a first flexural rigidity in the range of $3 \times 10^{-3}$ lb·in$^2$ to 50 lb·in$^2$; and
    a substantially elongated second body portion having a proximal end, a distal end, and a lumen formed therein extending between the proximal and distal ends, the proximal end of the second body portion being mounted to the distal end of the first body portion so that the lumens of the first and second body portions are fluidly connected to one another and the second body portion having a second flexural rigidity, wherein the second flexural rigidity is greater than approximately two times the first flexural rigidity and is in the range of $1 \times 10^{-4}$ to 50 lb·in$^2$ so that the second body portion is more rigid and less easily deformed than the first body portion
    wherein the first body portion is connected to a source of oxygenated blood and the cannula is configured to be used in minimally invasive surgical procedures, whereby an incision is created in a patient, and the first body portion is sufficiently selectively flexible to extend from the incision and be deformed out of the way of other surgical instruments that are inserted into the incision.

2. A cannula comprising:
    a first body portion having a proximal end, a distal end, and a lumen formed therein extending between the proximal and distal ends, the first body portion having a first flexural rigidity; and
    a substantially elongated second body portion having a proximal end, a distal end, and a lumen formed therein extending between the proximal and distal ends, the proximal end of the second body portion being mounted to the distal end of the first body portion so that the lumens of the first and second body portions are fluidly connected to one another and The second body portion having a second flexural rigidity, wherein the second flexural rigidity is greater than approximately two times the first flexural rigidity and is in the range of $1 \times 10^{-4}$ to $4 \times 10^{-3}$ lb·in$^2$ so that the second body portion is more rigid and less easily deformed than the first body portion
    wherein the first body portion is connected to a source of oxygenated blood and the cannula is configured to be used in minimally invasive surgical procedures, whereby an incision is created in a patient, and the first body portion is sufficiently selectively flexible to extend from the incision and be deformed out of the way of other surgical instruments that are inserted into the incision.

3. A cannula according to claim 2 wherein the first body portion is formed of polyvinyl chloride.

4. A cannula comprising:
    a first body portion having a proximal end, a distal end, and a lumen formed therein extending between the proximal and distal ends, the first body portion having a first flexural rigidity; and
    a substantially elongated second body portion having a proximal end, a distal end, and a lumen formed therein extending between the proximal and distal ends, the proximal end of the second body portion being mounted to the distal end of the first body portion so that the lumens of the first and second body portions are fluidly connected to one another and the second body portion having a second flexural rigidity, wherein the second flexural rigidity is greater than approximately two times the first flexural rigidity so that the second body portion is more rigid and less easily deformed than the first body portion, wherein the second flexural rigidity is approximately equal to $6 \times 10^{-3}$ lb·in$^2$; and
    wherein the cannula is configured to be used in minimally invasive surgical procedures, whereby an incision is created in a patient, and the first body portion is sufficiently selectively flexible to extend from the incision and be deformed out of the way of other surgical instruments that are inserted into the incision.

5. A cannula according to claim 4 wherein the first flexural rigidity is approximately equal to $3 \times 10^{-3}$ lb·in$^2$.

6. A cannula according to claim 5 wherein the second body portion is formed of urethane.

7. A cannula according to claim 6 wherein the first body portion is formed of polyvinyl chloride.

8. A cannula according to claim 4 wherein the first flexural rigidity is in the range of $3 \times 10^{-3}$ lb·in$^2$ to 50 lb·in$^2$.

9. A cannula according to claim 4 and further comprising a fluid connector provided on the proximal end of the first body portion, wherein the fluid connector is adapted to be fluidly connected to a source of fluid.

10. A cannula according to claim 9 and further comprising a bulbous projection provided on the distal end of the second body portion wherein the projection is adapted to be received inside a vessel.

11. A cannula according to claim 4 and further comprising a bulbous projection provided on the distal end of the second body portion wherein the projection is adapted to be received inside a vessel.

12. A cannula comprising:
a first body portion having a proximal end, a distal end, and a lumen formed therein extending between the proximal and distal ends, the first body portion having a first flexural rigidity;
a substantially elongated second body portion having a proximal end, a distal end, and a lumen formed therein extending between the proximal and distal ends, the proximal end of the second body portion being mounted to the distal end of the first body portion so that the lumens of the first and second body portions are fluidly connected to one another and the second body portion having a second flexural rigidity, wherein the second flexural rigidity is greater than approximately two times the first flexural rigidity so that the second body portion is more rigid and less easily deformed than the first body portion; and
a bulbous projection provided on the distal end of the second body portion wherein the projection is adapted TO be received inside a vessel;
wherein the first body portion is connected to a source of oxygenated blood and the cannula is configured to be used in minimally invasive surgical procedures, whereby an incision is created in a patient, and the first body portion is sufficiently selectively flexible to extend from the incision and be deformed out of the way of other surgical instruments that are inserted into the incision.

13. A vessel cannula for conducting fluid to or from a blood vessel comprising:
a first body portion having a proximal end, a distal end, and a lumen formed therein extending between the proximal and distal ends, the first body portion having a first flexural rigidity in the range of $1 \times 10^{-4}$ lb·in$^2$ to $4 \times 10^{-3}$ lb·in$^2$; and
a substantially elongated second body portion having a proximal end, a distal end, and a lumen formed therein extending between the proximal and distal ends, the proximal end of the second body portion being mounted to the distal end of the first body portion so that the lumens of the first and second body portions are fluidly connected to one another, and the second body portion having a second flexural rigidity in the range of $3 \times 10^{-3}$ lb·in$^2$ to 50 lb·in$^2$ so that the second body portion is more rigid and less easily deformed than the first body portion
wherein the first body portion is connected to a source of oxygenated blood and wherein the cannula is configured to be used in minimally invasive surgical procedures, whereby an incision is created in a patient, and the first body portion is sufficiently flexible to extend from the incision and be deformed out of the way of other surgical instruments that are inserted into the incision.

14. A cannula according to claim 13 wherein the second body portion is formed of urethane.

15. A cannula according to claim 13 wherein the first body portion is formed of polyvinyl chloride.

16. A cannula according to claim 13 and further comprising a fluid connector provided on the proximal end of the first body portion wherein the fluid connector is adapted to be fluidly connected to a source of fluid.

17. A cannula according to claim 13 and further comprising a bulbous projection provided on the distal end of the second body portion wherein the projection is adapted to be received inside a vessel.

18. A method of mounting a vessel cannula in a vessel comprising the steps of:
providing a cannula comprising:
a first body portion having a proximal end, a distal end, and a lumen formed therein, the lumen having an axis and extending between the proximal and distal ends, the first body portion having a first flexural rigidity; and
a second body portion having a proximal end, a distal end, and a lumen formed therein, the lumen having an axis and extending between the proximal and distal ends, the proximal end of the second body portion being mounted to the distal end of the first body portion so that the lumens of the first and second body portions are fluidly connected to one another, and the second body portion having a second flexural rigidity wherein the second flexural rigidity is greater than approximately two times the first flexural rigidity so that the second body portion is more rigid and less easily deformed than the first body portion;
providing an aperture, in the vessel;
grasping the second body portion of the cannula and then inserting the distal end of the second body portion into the vessel aperture;
positioning the first body portion of the cannula with respect to the second body portion so that the axes of the lumens of the first and second body portions are not aligned with one another; and
connecting an external oxygenator as a source of oxygenated blood to the first body portion.

19. A method of mounting a vessel cannula according to claim 18 and further comprising the steps of:
providing a source of fluid; and
fluidly connecting the proximal end of the first body portion of the cannula to the source of fluid.

20. A method of mounting a vessel cannula according to claim 19 wherein the vessel comprises the coronary artery and the fluid supplied by the source comprises oxygenated blood.

21. The method of mounting a vessel cannula according to claim 19 wherein the cannula further comprises a fluid connector provided on the proximal end of the first body portion, wherein the fluid connector is adapted to be fluidly connected to a source of fluid.

22. A method of mounting a vessel cannula according to claim 18 wherein a bulbous projection is provided on the distal end of the second body portion, the projection being adapted to be received inside a vessel.

23. A method of mounting a vessel cannula according to claim 22 wherein the step of grasping the second body portion of the cannula and then inserting the distal end of the second body portion into the vessel aperture further includes inserting the bulbous projection provided on the distal end of the second body portion into the vessel aperture.

24. A method of mounting a vessel cannula in a vessel comprising the steps of:

providing a cannula comprising:
- a first body portion having a proximal end, a distal end, and a lumen formed therein, the lumen having an axis and extending between the proximal and distal ends, the first body portion having a first flexural rigidity in the range of $1\times10^{-4}$ lb·in$^2$ to $4\times10^{-3}$ lb·in$^2$; and
- a second body portion having a proximal end, a distal end, and a lumen formed therein, the lumen having an axis and extending between the proximal and distal ends, the proximal end of the second body portion being mounted to the distal end of the first body portion so that the lumens of the first and second body portion are fluidly connected to one another, and the second body portion having a second flexural rigidity in the range of $3\times10^{-3}$ lb·in$^2$ to 50 lb·in$^2$ so that the second body portion is more rigid and less easily deformed than the first body portion;

providing an aperture in a vessel;

grasping the second body portion of the cannula and then inserting the distal end of the second body portion into the vessel through the vessel aperture; and positioning the first body portion of the cannula with respect to the second body portion so that the axes of the lumens of the first and second body portions are not aligned with one another; and connecting an external oxygenator as a source of oxygenated blood to the first body portion.

25. A method of mounting a vessel cannula according to claim 24 and further comprising the steps of:
   providing a source of fluid; and
   fluidly connecting the proximal end of the first body portion of the cannula to the source of fluid.

26. A method of mounting a vessel cannula according to claim 25 wherein the cannula further comprises a fluid connector provided on the proximal end of the first body portion, wherein the fluid connector is adapted to be fluidly connected to a source of fluid.

27. A method of mounting a vessel cannula according to claim 24 wherein a bulbous projection is provided on the distal end of the second body portion, the projection being adapted to be received inside a vessel.

28. A method of mounting a vessel cannula according to claim 27 wherein the step of grasping the second body portion of the cannula and then inserting the distal end of the second body portion into the vessel aperture further includes inserting the bulbous projection provided on the distal end of the second body portion into the vessel through the vessel aperture.

29. A method of mounting a vessel cannula according to claim 24 wherein the second body portion is formed of urethane.

30. A method of mounting a vessel cannula according to claim 24 wherein the first body portion is formed of polyvinyl chloride.

* * * * *